United States Patent
Kang

(10) Patent No.: US 8,961,656 B2
(45) Date of Patent: Feb. 24, 2015

(54) GAS HYDRATE INHIBITOR AND METHOD OF INHIBITING GAS HYDRATE FORMATION

(75) Inventor: Seong-Pil Kang, Daejeon (KR)

(73) Assignee: Korea Institute of Energy Research, Daejeon (KR)

( * ) Notice: Subject to any disclaimer, the term of this patent is extended or adjusted under 35 U.S.C. 154(b) by 867 days.

(21) Appl. No.: 13/169,538

(22) Filed: Jun. 27, 2011

(65) Prior Publication Data

US 2011/0319682 A1 Dec. 29, 2011

(30) Foreign Application Priority Data

Jun. 28, 2010 (KR) .......................... 10-2010-0061000

(51) Int. Cl.
| | | |
|---|---|---|
| C07C 7/20 | (2006.01) | |
| C07D 207/08 | (2006.01) | |
| C07F 5/02 | (2006.01) | |
| C07D 207/06 | (2006.01) | |
| C09K 8/52 | (2006.01) | |
| C10L 3/10 | (2006.01) | |

(52) U.S. Cl.
CPC ............ *C07D 207/08* (2013.01); *C07D 207/06* (2013.01); *C09K 8/52* (2013.01); *C09K 2208/22* (2013.01); *C10L 3/107* (2013.01)
USPC ........ 95/153; 585/15; 585/2; 585/3; 548/574; 548/405

(58) Field of Classification Search
CPC .. C08K 5/3415; C08L 39/04; C09K 2208/22; C09K 8/52; C10L 3/107
USPC ................ 95/153; 585/15, 2, 3; 548/405, 574
See application file for complete search history.

(56) References Cited

U.S. PATENT DOCUMENTS

2010/0216675 A1* 8/2010 Habeeb ......................... 508/279

FOREIGN PATENT DOCUMENTS

KR 1020100028976 A 3/2010

OTHER PUBLICATIONS

Xiao et al., "Dual Function Inhibitors for Methane Hydrate," Chemical Engineering Science 64, 2009, pp. 1522-1527.*
Kim et al., "Tuning Ionic Liquids for Hydrate Inhibition," Chem. Commun., 2011, 47, 6341-6343.*
Article—Xiao et al., "Dual Function Inhibitors for Methane Hydrate," *Chemical Engineering Science 64*, 2009, pp. 1522-1527.

* cited by examiner

*Primary Examiner* — Duane Smith
*Assistant Examiner* — Cabrena Holecek
(74) *Attorney, Agent, or Firm* — Dority & Manning, P.A.

(57) ABSTRACT

The present invention relates to an ionic liquid compound that inhibits a formation of a gas hydrate. The compound of the present invention changes an equilibrium temperature and pressure of a gas hydrate in small quantity into a lower temperature and/or a higher pressure, and simultaneously retards the formation of the gas hydrate under the same environment. Thus, the compound of the present invention is used in oil and natural gas industries to effectively inhibit or delay the formation of the gas hydrate under the condition having a low temperature and a high pressure.

11 Claims, 2 Drawing Sheets

GAS HYDRATE INHIBITOR AND METHOD OF INHIBITING GAS HYDRATE FORMATION

CROSS-REFERENCE TO RELATED APPLICATION

This application claims priority under 35 U.S.C. §119 to Korean Patent Application No. 10-2010-0061000, filed on Jun. 28, 2010 in the Korean Intellectual Property Office KIPO, the content of which is herein incorporated by reference in its entirety.

BACKGROUND OF THE INVENTION

1. Field of the Invention

The present invention relates to a gas hydrate inhibitor, a composition including the gas hydrate inhibitor and a method of inhibiting a formation of a gas hydrate.

2. Description of the Related Art

Gas hydrates are ice-like solid compounds formed by entrapping "guest" molecules, such as methane, ethane, propane, carbon dioxide, nitrogen and the like, in a three-dimensional lattice structure built by hydrogen bonds of "host" water molecules. In general, the gas hydrates are formed and stably exist at low-temperature and high-pressure conditions.

Any solids in oil and gas industries are at least a nuisance for production, transport and processing of fluids. Thus, it is common for the gas hydrates to cause blockage problem of pipelines and other facilities, resulting in shutdown, loss of production, and risk of release of hydrocarbons into the environment. Consequently, the gas hydrates have attracted substantial interest on the suitable inhibition methods, in oil and gas industries in particular. Production of oil and natural gas and transport of the fluids are usually carried out in deep ocean and thus the fluid passes through low temperature and high pressure conditions where the formation of the gas hydrate is favored. These produced fluids have some amount accompanying water and dominantly contain gaseous and liquid hydrocarbons, which results in the formation of the solid gas hydrates. Aforementioned gas hydrate solids deposit on the surface of the pipelines, valves, and equipment so as to obstruct the transport and further processing of the fluids. In addition, the removal of the gas hydrates from the occurred parts requires a lot of time and cost which results in a loss of production during the remedy. For this reason, lots of efforts have been made to inhibit the formation of the gas hydrates in oil and natural gas industries.

Accordingly, the efficient and cost-effective inhibitors for the gas hydrate formation have been developed. However, the conventional inhibitors cannot sufficiently control and inhibit the formation of the gas hydrates. For example, too much amount of inhibitors is needed or insufficient retarding for the gas hydrate formation is happened. Thus, it is required a new gas hydrate which yield enhanced results over conventional gas hydrate inhibitors.

SUMMARY OF THE INVENTION

An aspect of the present invention provides a gas hydrate inhibitor comprising an ionic liquid compound represented by Chemical Formula 1:

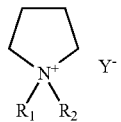

[Chemical Formula 1]

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain of an aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$.

In some example embodiments of the present invention, $R_1$ may be a methyl group, an ethyl group or a propyl group and $R_2$ may be a butyl group, a pentyl group, a hexyl group, a heptyl group, a hydroxymethyl group, a hydroxyethyl group, or a hydroxypropyl group.

In some example embodiments of the present invention, $R_1$ may be a methyl group, and $R_2$ is a butyl group, a pentyl group, a hydroxymethyl group, a hydroxyethyl group, or a hydroxypropyl group.

In some example embodiments of the present invention, $Y^-$ may be $Cl^-$ or $BF_4^-$.

In some example embodiments of the present invention, the compound represented by Chemical Formula 1 may be N-hydroxyethyl-N-methylpyrrolidinium chloride.

In some example embodiments of the present invention, the compound represented by Chemical Formula 1 may be N-butyl-N-methylpyrrolidinium tetrafluoroborate.

In some example embodiments of the present invention, the compound represented by Chemical Formula 1 may be N-hydroxyethyl-N-methylpyrrolidinium tetrafluoroborate or a mixture thereof.

Another aspect of the present invention provides a composition for inhibiting a gas hydrate, comprising a compound represented by Chemical Formula 1:

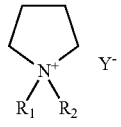

[Chemical Formula 1]

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain of an aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$.

In some example embodiments of the present invention, the composition may include the compound represented by Chemical Formula 1 in a range of about 1.01 wt % to about 30 wt % with respect to a total weight of water present in a place where the formation of the gas hydrate is inhibited.

Still another aspect of the present invention provides a method of inhibiting a formation of a gas hydrate using a compound represented by Chemical Formula 1:

[Chemical Formula 1]

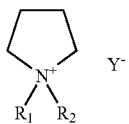

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$.

According to the present invention, the compound of the present invention can effectively inhibit a formation of a gas hydrate. That is, the compound of the present invention changes equilibrium conditions of the gas hydrate to allow the gas hydrate to be formed at a lower temperature and/or higher pressure and delays an induction time of a gas hydrate formation under the same temperature and pressure, thus inhibiting the formation of the gas hydrate in a small quantity.

BRIEF DESCRIPTION OF THE DRAWINGS

The above and other objects, features, and advantages of the present invention will be more clearly understood from the following detailed description taken in conjunction with the accompanying drawings, in which.

DESCRIPTION OF THE PREFERRED EMBODIMENTS

Figure 1:
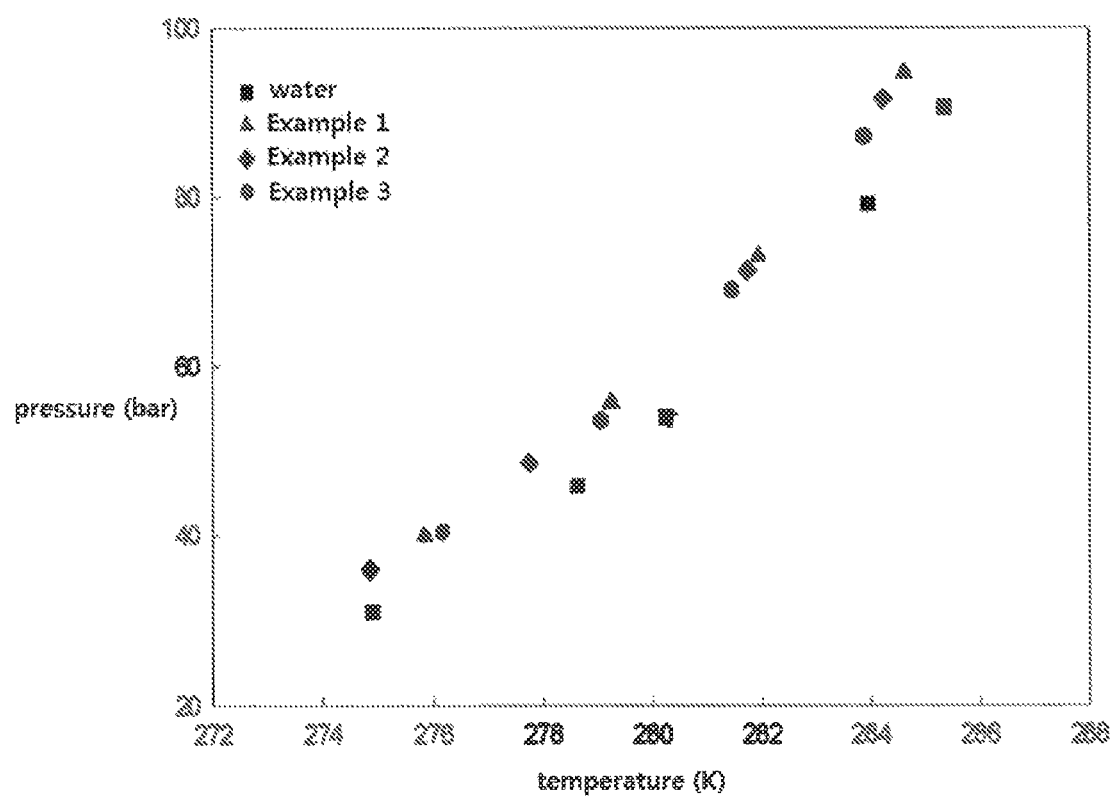
FIG. 1 is a graph showing a change in equilibrium dissociation conditions of a methane hydrate according to the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present invention provides a gas hydrate inhibitor, comprising a compound represented by Chemical Formula 1:

[Chemical Formula 1]

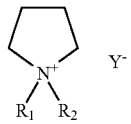

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$.

In accordance with the present invention, the gas hydrate inhibitor means a compound that can prevent or delay the formation of the gas hydrate.

In accordance with the present invention, the compound represented by Chemical Formula 1 can prevent or delay the formation of the gas hydrate regardless of the kind of gas. That is, the compound represented by Chemical Formula 1 can prevent or delay the formation of the gas hydrate regardless of the kind of gas entrapped inside a cavity formed by hydrogen bonded water molecules. Examples of the gas may include hydrocarbons having a low-molecular-weight. For example, the gas may include methane, ethane, propane, butane, pentane, or a mixture thereof.

The compound represented by Chemical Formula 1 may be an ionic liquid compound. The ionic liquid compound may be a salt in a liquid state and have a melting point below about 100° C. The ionic liquid compound may include a cation and an anion. In accordance with the present invention, the compound represented by Chemical Formula 1 includes pyrrolidinium as the cation, and includes $OH^-$, $Cl^-$, $Br^-$, $I^-$, $CH_3COO^-$, $NO_3^-$ or $BF_4^-$ as an anion.

The compound represented by Chemical Formula 1 may function as both a thermodynamic inhibitor and a kinetic inhibitor in the formation of the gas hydrate.

In the formation of the gas hydrate, the thermodynamic inhibitor may change an equilibrium dissociation condition of the gas hydrate. That is, the thermodynamic inhibitor, which shifts an equilibrium dissociation curve of the gas hydrate to a lower temperature and/or a higher pressure, may generally enable the gas hydrate to be formed at a lower temperature and/or a higher pressure.

Further, in the formation of the gas hydrate, the kinetic inhibitor may retard a gas hydrate nucleation and/or growth at the same temperature and at the same pressure without changing the equilibrium condition of the gas hydrate. That is, the kinetic inhibitor may delay an induction time of the gas hydrate formation at the same temperature and at the same pressure.

The compound represented by Chemical Formula 1 may serve as both the thermodynamic inhibitor and the kinetic inhibitor in the formation of the gas hydrate. The compound represented by Chemical Formula 1 may change the equilibrium condition of the gas hydrate so that the gas hydrate may be formed at a lower temperature and/or a higher pressure. Further, the compound represented by Chemical Formula 1 may retard the formation of the gas hydrate at the same temperature and at the same pressure by slowing down the gas hydrate nucleation and/or growth and thus the induction time of the gas hydrate formation may be delayed. Therefore, when the compound represented by Chemical Formula 1 is used in oil and natural gas industries, the gas hydrate may be formed at a lower temperature and/or a higher pressure and also the formation of the gas hydrate may be delayed at the same temperature and at the same pressure to effectively inhibit the formation of the gas hydrate in a small quantity for production, processing and transportation of oil and natural gas.

In accordance with the present invention, the compound represented by Chemical Formula 1 may decrease the equilibrium temperature of the gas hydrate by about 1.3~1.7K at the same pressure, and may delay the induction time of the gas hydrate formation by a maximum of about 6 hours at the same temperature and at the same pressure.

In the compound represented by Chemical Formula 1 of the present invention, $R_1$ may be a methyl group, an ethyl group, or a propyl group, and $R_2$ may be a butyl group, a pentyl group, a hexyl group, a heptyl group, a hydroxymethyl group, a hydroxyethyl group, or a hydroxypropyl group. Preferably, $R_1$ may be a methyl group, and $R_2$ may be a butyl group, a pentyl group, a hydroxymethyl group, a hydroxyethyl group, or a hydroxypropyl group.

Further, in the compound represented by Chemical Formula 1 of the present invention, $Y^-$ may be $Cl^-$ or $BF_4^-$.

In accordance with the present invention, the compound represented by Chemical Formula 1 may be selected from compounds represented by Chemical formulae 2 to 4.

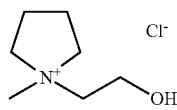

[Chemical formula 2]

The compound represented by Chemical Formula 2 may be N-hydroxyethyl-N-methylpyrrolidinium chloride.

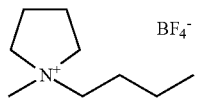

[Chemical formula 3]

The compound represented by Chemical Formula 3 may be N-butyl-N-methylpyrrolidinium tetrafluoroborate.

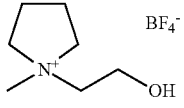

[Chemical formula 4]

The compound represented by Chemical Formula 4 may be N-hydroxyethyl-N-methylpyrrolidinium tetrafluoroborate.

The present invention provides a composition for inhibiting a gas hydrate, comprising a compound represented by Chemical Formula 1:

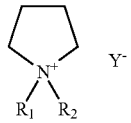

[Chemical Formula 1]

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain of an aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$.

In accordance with the present invention, the composition may include solvent. The solvent may include water, an alcohol of $C_4$~$C_6$, a glycol of $C_4$~$C_6$, an ether of $C_4$~$C_{10}$, an ester of $C_3$~$C_{10}$, a ketone of $C_3$~$C_{10}$, or a mixture thereof. Preferably, the solvent may be water.

In accordance with the present invention, the composition may include the compound represented by Chemical Formula 1 in a range of about 0.01~about 30 wt % with respect to the total weight of a solvent present in a place where the formation of the gas hydrate is inhibited. When the composition contains about 0.01~about 30 wt % of the compound represented by Chemical Formula 1, the formation of the gas hydrate may be effectively inhibited, which is economically advantageous. When the amount of the compound represented by Chemical Formula 1 is more than about 30 wt % in the composition, it is too expensive to practically apply the composition to oil and natural gas industries. Particularly, when the composition is applied to pipelines of oil and natural gas industries, the composition including the compound represented by Chemical Formula 1 may cause a corrosion of the pipelines, a generation of foam or a precipitate on the pipeline. Therefore, the composition may include the compound represented by Chemical Formula 1 at a concentration of about 0.01~about 30 wt %, and preferably about 0.05~about 11 wt %. For example, the composition may include about 0.01~about 30 wt % of the compound represented by Chemical Formula 1 with respected to the total weight of a water present in the place where the formation of the gas hydrate is inhibited.

In accordance with the present invention, the composition may include another gas hydrate inhibitor together with the compound represented by Chemical Formula 1. For example, the composition may include a methanol, ethanol, n-propanol, isopropanol, ethylene glycol, propylene glycol, potassium formate, methylacrylamide, acrylamide, N-butylacrylamide, sodium chloride, polyvinylidene, or a mixture thereof together with the compound represented by Chemical Formula 1 as a gas hydrate inhibitor.

The present invention provides a method of inhibiting a formation of a gas hydrate using a compound represented by Chemical Formula 1:

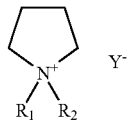

[Chemical Formula 1]

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$.

In accordance with the present invention, the compound represented by Chemical Formula 1 may be introduced into a place where the formation of the gas hydrate is undesirable to change an equilibrium condition of the gas hydrate into a lower temperature and/or a higher pressure. Thus, the compound represented by Chemical Formula 1 may effectively inhibit the formation of the gas hydrate in a place which has a lower temperature and/or a higher pressure than those of the equilibrium condition of the gas hydrate.

In accordance with the present invention, the compound represented by Chemical Formula 1 may be introduced into a place where the formation of the gas hydrate is undesirable to retard the formation of the gas hydrate at a same temperature and a same pressure. Thus, the compound represented by Chemical Formula 1 may effectively delay an induction time of the gas hydrate formation in a place which has a temperature and a pressure at which the formation of the gas hydrate may be favored.

That is, when the compound represented by Chemical Formula 1 is used, the gas hydrate may be formed at a lower temperature and/or a higher pressure and thus the formation of the gas hydrate may be basically inhibited. Further, the formation of the gas hydrate may be also delayed under a temperature and a pressure at which the formation of the gas hydrate may be favored.

In accordance with the present invention, the compound represented by Chemical Formula 1 may be directly injected into a place where the formation of the gas hydrate is inhibited. In this case, the quantity of the compound represented by Chemical Formula 1 directly injected into the place may be in a range of about 0.01~about 30 wt % with respect to the total weight of water present in the place where the formation of the gas hydrate is inhibited.

In accordance with the present invention, the compound represented by Chemical Formula 1 may be used after the compound represented by Chemical Formula 1 is dissolved in a solvent. The solvent may include water, an alcohol of $C_4\text{~}C_6$, a glycol of $C_4\text{~}C_6$, an ether of $C_4\text{~}C_{10}$, an ester of $C_3\text{~}C_{10}$, a ketone of $C_3\text{~}C_{10}$, or a mixture thereof. Preferably, the solvent may be water.

When the compound represented by Chemical Formula 1 is dissolved in the solvent, the compound represented by Chemical Formula 1 may be dissolved at a concentration of about 0.01~about 30 wt % with respect to the total weight of a solvent present in the place where the formation of the gas hydrate is inhibited. For example, the compound represented by Chemical Formula 1 may be included in a concentration of about 0.01~about 30 w % with respect to the total weight of water present in the place where the formation of the gas hydrate is inhibited.

In accordance with the present invention, another compound may be additionally used as a gas hydrate inhibitor together with the compound represented by Chemical Formula 1. For example, a methanol, ethanol, n-propanol, isopropanol, ethylene glycol, propylene glycol, potassium formate, methylacrylamide, acrylamide, N-butylacrylamide, sodium chloride, polyvinylidene, or a mixture thereof may be used together with the compound represented by Chemical Formula 1 as a gas hydrate inhibitor.

In accordance with the present invention, the compound represented by Chemical Formula 1 may be any one of compounds represented by Chemical Formulae 2 to 4 below.

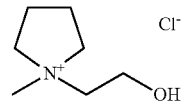

[Chemical Formula 2]

The compound represented by Chemical Formula 2 may be N-hydroxyethyl-N-methylpyrrolidinium chloride.

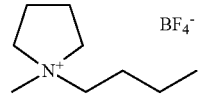

[Chemical Formula 3]

The compound represented by Chemical Formula 3 may be N-butyl-N-methylpyrrolidinium tetrafluoroborate.

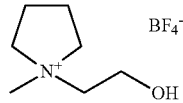

[Chemical Formula 4]

The compound represented by Chemical Formula 4 may be N-hydroxyethyl-N-methylpyrrolidinium tetrafluoroborate.

In accordance with the present invention, one or more of the compounds represented by Chemical Formula 1 may be used. For example, the formation of the gas hydrate may be inhibited using an aqueous solution including both N-butyl-N-methylpyrrolidinium tetrafluoroborate represented by Chemical Formula 3 and N-hydroxyethyl-N-methylpyrrolidinium tetrafluoroborate represented by Chemical Formula 4.

Hereinafter, the present invention will be described in more detail with reference to the following Examples. However, the following Examples are set forth to more easily understand the present invention, and the scope of the present invention is not limited thereto.

The following $^1$H-NMR data are measured using Advance 400FT-NMR (400 MHz) manufactured by Barker Co., Ltd.

Example 1

Preparation of N-hydroxyethyl-N-methylpyrrolidinium chloride

About 200 mL of acetonitrile (manufactured by Junsei Co., Ltd. in Japan) was mixed with about 52.7 mL (0.5 mol) of methylpyrrolidone (manufactured by Fluka Co., Ltd.) under a nitrogen atmosphere to form a liquid mixture. Subsequently, about 36.5 mL (0.55 mol) of 2-chloroethanol (manufactured by Aldrich Co., Ltd.) was added to the liquid mixture drop by drop to form a mixed solution. Subsequently, the mixed solution was stirred at about 65° C. for about 48 hours under a nitrogen atmosphere, and was then stored at about 4° C. for about 12 hours to form crystals. After a supernatant was removed from the mixed solution, the crystals were dried at a temperature of about 35° C. and a pressure of about 0.2 atm for about 12 hours using a vacuum evaporator to remove a solvent therefrom. Subsequently, in order to remove impurity, the dried crystals were dissolved in about 100 mL of acetone, and were then stirred at a temperature of about 25° C. and a pressure of about 1 atm for about 30 minutes to form a solution. The solution was stored at about 4° C. for about 12 hours to form crystals again. After a supernatant was removed from the solution, the crystals were dried at a temperature of about 35° C. and a pressure of about 0.2 atm for about 12 hours using a vacuum evaporator. These processes were repeatedly conducted three times to obtain N-hydroxyethyl-N-methylpyrrolidinium chloride at a yield of about 60%.

$^1$H-NMR (400 MHz, D$_2$O): δ 4.698 (s, 2H), 3.891~3.854 (m, 2H), 3.438~3.335 (m, 7H), 2.929 (s, OH), 2.042 (s, 4H)

Example 2

Preparation of N-hydroxyethyl-N-methylpyrrolidinium tetrafluoroborate

About 200 mL of acetonitrile (manufactured by Junsei Co., Ltd. in Japan) was mixed with about 52.7 mL (0.5 mol) of methylpyrrolidone (manufactured by Fluka Co., Ltd.) under a nitrogen atmosphere to form a liquid mixture. Subsequently, about 36.5 mL (0.55 mol) of 2-chloroethanol (manufactured by Aldrich Co., Ltd.) was added to the liquid mixture drop by drop to form a mixed solution. Subsequently, the mixed solution was stirred at about 65° C. for about 48 hours under a nitrogen atmosphere, and was then stored at about 4° C. for about 12 hours to form crystals. After a supernatant was removed from the mixed solution, the crystals were dried at a temperature of about 35° C. and a pressure of about 0.2 atm for about 12 hours using a vacuum evaporator to remove a solvent therefrom. Subsequently, in order to remove impurities, the dried crystals were dissolved in about 100 mL of acetone, and then were stirred at a temperature of about 25° C. and a pressure of about 1 atm for about 30 minutes to form a solution. The solution was stored at about 4° C. for about 12 hours to form crystals again. After a supernatant was removed from the solution, the crystals were dried at a temperature of about 35° C. and a pressure of about 0.2 atm for about 12 hours using a vacuum evaporator. These processes were repeatedly conducted three times to obtain N-hydroxyethyl-N-methylpyrrolidinium chloride at a yield of about 75%.

Subsequently, about 36.9 g (0.3 mol) of the obtained N-hydroxyethyl-N-methylpyrrolidinium chloride and about 32.3 g (0.3 mol) of sodium tetrafluoroborate were dissolved in about 200 mL of acetone, and were then stirred at a temperature of about 25° C. and a pressure of about 1 atm for about 48 hours under a nitrogen atmosphere to form a mixed solution containing sodium chloride. The mixed solution was filtered by a filter paper to remove sodium chloride therefrom to obtain a liquid. Then, the obtained liquid, about 50 mL of dichloromethane, and about 0.5 mL of distilled water were shaken in a separating funnel for about 10 minutes and thus uniformly mixed with each other to form a mixed solution, and then the mixed solution was left at a temperature of 25° C. and a pressure of about 1 atm for about 48 hours. When the mixed solution was layer-separated in the separating funnel according to a density, the liquid located in a lower portion of the separating funnel was removed, and the liquid located in an upper portion thereof was obtained. These processes were repeatedly conducted three times to obtain a final liquid. The final liquid was left in a vacuum oven at about 35° C. for about 48 hours to further remove water therefrom, thereby obtaining N-hydroxyethyl-N-methylpyrrolidinium tetrafluoroborate at a yield of about 65%.

$^1$H-NMR (400 MHz, DMSO): δ 5.3~5.28 (t, 2H), 3.83~3.82 (q, 2H), 3.51~3.39 (m, 7H), 2.08~2.07 (m, 4H)

Example 3

Preparation of N-butyl-N-methylpyrrolidinium tetrafluoroborate

About 200 mL of acetonitrile (manufactured by Junsei Co., Ltd. in Japan) was mixed with about 523 mL (0.5 mol) of methylpyrrolidone (manufactured by Fluka Co., Ltd.) under a nitrogen atmosphere to form a liquid mixture. Subsequently, about 58.6 mL (0.55 mol) of 2-bromobutane (manufactured by Aldrich Co., Ltd.) was added into the liquid mixture drop by drop to form a mixed solution. Subsequently, the mixed solution was stirred at about 65° C. for about 48 hours under a nitrogen atmosphere, and was then stored at about 4° C. for about 12 hours to form crystals. After a supernatant was removed from the mixed solution, the crystals were dried at a temperature of about 35° C. and a pressure of about 0.2 atm for about 12 hours using a vacuum evaporator to remove a solvent therefrom. Subsequently, in order to remove impurities, the dried crystals were dissolved in about 100 mL of acetone, and were then stirred at a temperature of about 25° C. and a pressure of about 1 atm for about 30 minutes to form a solution. The solution was left at 4° C. for about 12 hours to form crystals again. After a supernatant was removed from the solution, the crystals were dried at a temperature of about 35° C. and a pressure of about 0.2 atm for about 12 hours using a vacuum evaporator. These processes were repeatedly conducted three times to obtain N-butyl-N-methylpyrrolidinium bromide at a yield of about 60%.

Subsequently, about 24.8 g (0.3 mol) of the obtained N-butyl-N-methylpyrrolidinium bromide and about 32.3 g (0.3 mol) of sodium tetrafluoroborate were dissolved in about 200 mL of acetone, and were then stirred at a temperature of about 25° C. and a pressure of about 1 atm for about 48 hours under a nitrogen atmosphere to form a mixed solution containing sodium bromide. The mixed solution was filtered by a filter paper to remove sodium bromide therefrom to obtain a liquid. Then, the obtained liquid, about 50 mL of dichloromethane, and about 0.5 mL of distilled water were shaken in a separating funnel for about 10 minutes and thus uniformly mixed with each other to form a mixed solution, and then the mixed solution was left at a temperature of about 25° C. and a pressure of about 1 atm for about 48 hours. When the mixed solution was layer-separated in the separating funnel according to a density, the liquid located in a lower portion of the separating funnel was removed, and the liquid located in an upper portion thereof was obtained. These processes were repeatedly conducted three times to obtain a final liquid. The final liquid was left in a vacuum oven at about 35° C. for about 48 hours to further remove water therefrom, thereby obtaining N-butyl-N-methylpyrrolidinium tetrafluoroborate at a yield of about 45%.

$^1$H-NMR (400 MHz, D2O): δ 3.39 (s, 4H), 3.24~3.20 (m, 2H), 2.93 (s, 3H), 2.10 (s, 4H), 1.71~1.63 (m, 2H), 1.31~1.25 (m, 2H), 0.86~0.82 (t, 3H)

Experimental Example 1

Ascertainment of Change in Phase Equilibrium Temperature and Pressure of Methane Hydrate 1. Providing an Experimental System A high-pressure reactor having an inner volume of about 350 cc and made of stainless steel was provided. The high-pressure reactor was disposed in a water tank provided at the outside thereof with a cooler for a temperature control. A sapphire observation window was provided over the high-temperature reactor in order to observe whether a hydrate was formed and a pressure transducer and a thermocouple was provided in the high-temperature reactor in order to measure the temperature and pressure in the high-pressure reactor. This experimental system including the high-pressure reactor and the water tank and measuring the phase equilibrium temperature and pressure of the hydrate in the formation and dissociation thereof is disclosed in the paper "Hydrate phase equilibria of the guest mixtures containing $CO_2$, $N_2$ and tetrahydrofuran (Fluid Phase Equilibria 185 (2001), 101-109)".

2. Measuring the Phase Equilibrium Temperature and Pressure of a Methane Hydrate in the Dissociation Thereof An aqueous solution containing about 10 wt % of N-hydroxyethyl-N-Methylpyrrolidinium chloride in Example 1 was prepared. About 90 g of the aqueous solution was put into the high-pressure reactor, and then the high-pressure reactor was tightly closed. Air remaining in the high-pressure reactor was removed, and then a methane gas was injected into the high-pressure reactor until the pressure in the high-pressure reactor was about 70 atm. Subsequently, the high-pressure reactor was put into the temperature-controllable water tank, and then the pressure and temperature in the high-pressure reactor were measured in real time using a pressure gauge and a thermometer connected to the high-pressure reactor.

The aqueous solution in the high-pressure reactor was stirred, and simultaneously the water tank was cooled to reduce the temperature of the high-pressure reactor. When the pressure in the high-pressure reactor was rapidly dropped and the temperature thereof was increased, that means the formation of gas hydrate had occurred. After that, the system was remained as it was to allow the growth of gas hydrate crystals. Thereafter, whether or not the aqueous solution in the high-pressure reactor was completely converted into the methane hydrate was observed through the sapphire observation window.

After the aqueous solution in the high-pressure reactor was completely converted into the methane hydrate, the water tank was heated at a rate of about 0.2° C./hr. According to the temperature increase, methane captured in the gas hydrate was retrieved therefrom, and simultaneously the pressure in the high-pressure reactor was continuously increased. The increase of the pressure in the high-pressure reactor becomes slow when methane hydrate is completely dissociated. Thus the pressure and temperature in the high-pressure reactor were measured at the time that the increase rate of the pressure in the high-pressure reactor started to decrease so that the phase equilibrium temperature and pressure of the methane hydrate were measured.

Further, the phase equilibrium temperature and pressure of the methane hydrate were measured in the same manner as above using N-hydroxyethyl-N-methylpyrrolidinium tetrafluoroborate prepared in Example 2 and N-butyl-N-methylpyrrolidinium tetrafluoroborate prepared in Example 3 instead of using N-hydroxyethyl-N-methylpyrrolidinium chloride prepared in Example 1. Further, the phase equilibrium temperature and pressure of the methane hydrate were measured in the same manner as above using pure water. The phase equilibrium temperatures and pressures of the methane hydrate, measured using the compounds of Examples 1, 2, 3 or water, are illustrated in FIG. 1.

As illustrated in FIG. 1, the methane hydrate was formed at a higher pressure in the aqueous solutions containing one of compounds of Examples 1 to 3 than in the pure water under the same temperature. Further, the methane hydrate was formed at a lower temperature in the aqueous solutions containing one of compounds of Examples 1 to 3 than in the pure water under the same pressure. Therefore, when the compounds of Examples 1, 2 or 3 were applied into oil and natural gas industries, the formation of the methane hydrate was inhibited until the pressure and temperature reached a lower temperature and/or higher pressure, compared to those of the equilibrium conditions in case that the compounds of Examples 1, 2 or 3 were not applied.

Experimental Example 2

Measuring a Delay of a Formation of a Methane Hydrate

1. Providing an Experimental System

An experimental system including a high-pressure reactor and a water tank was provided as used in Experimental Example 1.

2. Measuring an Induction Time of a Methane Hydrate Formation

An aqueous solution containing about 10 wt % of N-hydroxyethyl-N-methylpyrrolidinium chloride in Example 1 was prepared. About 90 g of the aqueous solution was put into a high-pressure reactor, and then the high-pressure reactor was tightly closed. Air remaining in the high-pressure reactor was removed, and then a methane gas was injected into the high-pressure reactor until the pressure in the high-pressure reactor was about 70 atm.

Subsequently, the high-pressure reactor was put into the temperature-controllable water tank, and then the pressure and temperature in the high-pressure reactor were measured in real time using a pressure gauge and a thermometer connected to the high-pressure reactor.

After the temperature in the high-pressure reactor was set to about 0.5° C., the aqueous solution was started to stir the content continuously at a rotation speed of about 400 rpm to uniformly disperse N-hydroxyethyl-N-methylpyrrolidinium chloride in the aqueous solution while the temperature of the aqueous solution was maintained constant.

The change of the pressure and temperature in the high-pressure reactor was continuously measured. When a rapid temperature increase and a pressure drop thereof were observed, a time from the beginning of stirring to this time was measured and the time from stirrer start to this time was defined as an induction time of a methane hydrate formation.

The induction time of the methane hydrate fat nation was measured in the same manner as above using N-hydroxyethyl-N-methylpyrrolidinium tetrafluoroborate prepared in Example 2 or N-butyl-N-methylpyrrolidinium tetrafluoroborate prepared in Example 3 instead of using N-hydroxyethyl-N-methylpyrrolidinium chloride prepared in Example 1. Further, the induction time of the methane hydrate formation was measured in the same manner as above using 1-ethyl-3-methylimidazolinium tetrafluoroborate (manufactured by C-RTI Co., Ltd.) as a control group instead of using N-hydroxyethyl-N-methylpyrrolidinium chloride prepared in Example 1. The induction times of the methane hydrate formation, measured using the compounds of Examples 1, 2, 3 or 1-ethyl-3-methylimidazolinium tetrafluoroborate, are illustrated in FIG. 2.

Figure 2:
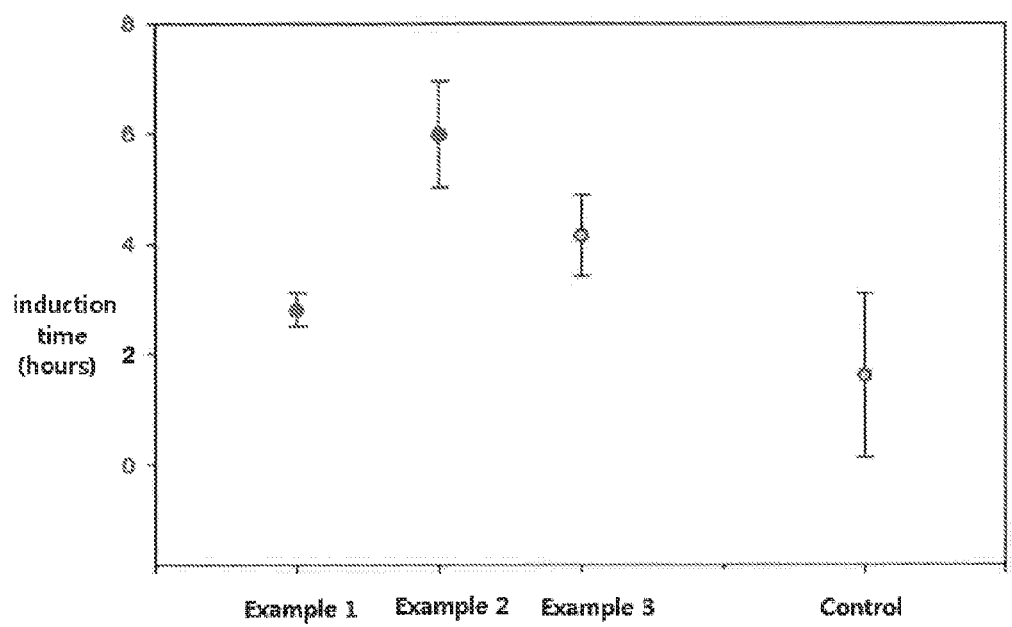
FIG. 2 is a graph showing a delay of a methane hydrate formation according to the present invention.

As illustrated in FIG. 2, when the compounds of Examples 1 to 3 were used, the induction times of the methane hydrate formation was delayed by two hours or more. In particular, when the compound of Example 2 was used, the induction time of the methane hydrate formation was delayed by about six hours, thus effectively retarding the formation of the methane hydrate. In contrast, when 1-ethyl-3-methylimidazolinium tetrafluoroborate was used, the induction time of the methane hydrate formation was delayed by less than two hours.

Therefore, when the compounds of Examples 1, 2 or 3 was applied to the place having a predetermined temperature and pressure which the formation of the methane hydrate is favored, the formation of the methane hydrate can be effectively delayed for a predetermined time.

As seen in the above Experimental Examples, the compounds of Examples 1 to 3 may change the equilibrium conditions of the gas hydrate into a lower temperature and/or higher pressure. Therefore, it is confirmed that the compound represented by Chemical Formula 1 of the present invention may basically inhibit the formation of the gas hydrate in oil and natural gas industries where the operating temperature and pressure favor the formation of the gas hydrate such as sea bottom.

Additionally, the compounds of Examples 1 to 3 may delay the induction time of the gas hydrate formation at the same temperature and the same pressure. Therefore, it is confirmed that the compound represented by Chemical Formula 1 of the present invention may effectively retard the formation of the gas hydrate in oil and natural gas industries where the operating temperature and pressure favor the formation of the gas hydrate such as sea bottom.

The foregoing is illustrative of the present invention and is not to be construed as limiting thereof. Although a few example embodiments of the present invention have been described, those skilled in the art will readily appreciate that many modifications are possible in the example embodiments without materially departing from the novel teachings and advantages of this invention. Accordingly, all such modifications are intended to be included within the scope of the present invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The present invention is defined by the following claims, with equivalents of the claims to be included therein.

What is claimed is:

1. A gas hydrate inhibitor, comprising a compound represented by Chemical Formula 1:

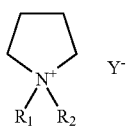

[Chemical Formula 1]

wherein the compound represented by Chemical Formula 1 is N-hydroxyethyl-N-methylpyrrolidinium chloride or N-hydroxyethyl-N-methylpyrrolidinium tetrafluoroborate.

2. A composition for inhibiting a formation of a gas hydrate, comprising a compound represented by Chemical Formula 1:

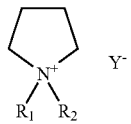

[Chemical Formula 1]

wherein the compound represented by Chemical Formula 1 is N-hydroxyethyl-N-methylpyrrolidinium chloride or N-hydroxyethyl-N-methylpyrrolidinium tetrafluoroborate, wherein the composition further comprises a solvent, wherein the solvent is water.

3. The composition of claim 2, wherein the compound represented by Chemical Formula 1 is included in a range of about 0.001 wt % to about 30 wt % with respect to the total weight of water.

4. A method of inhibiting a gas hydrate formation using a compound represented by Chemical Formula 1:

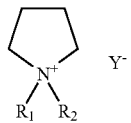

[Chemical Formula 1]

wherein $R_1$ and $R_2$ are each independently a straight chain or branched chain alkyl group of $C_1$ to $C_7$, a straight chain or branched chain hydroxyalkyl group of $C_1$ to $C_7$, a straight chain or branched chain of an aminoalkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$, the method comprising injecting the compound into a place to inhibit the formation of the gas hydrate.

5. The method of claim 4, wherein the compound is dissolved in water prior to using the compound represented by Chemical Formula 1.

6. The method of claim 4, wherein $R_1$ is a methyl group, an ethyl group, or a propyl group, and $R_2$ is a butyl group, a pentyl group, a hexyl group, a heptyl group, a hydroxymethyl group, a hydroxyethyl group, or a hydroxypropyl group.

7. The method of claim 4, wherein $R_1$ is a methyl group, and $R_2$ is a butyl group, a pentyl group, a hydroxymethyl group, a hydroxyethyl group, or a hydroxypropyl group.

8. The method of claim 4, wherein $Y^-$ is $Cl^-$ or $BF_4^-$.

9. A method of inhibiting a gas hydrate formation using a composition comprising a compound represented by Chemical Formula 1:

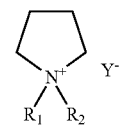

[Chemical Formula 1]

wherein $R_1$ and $R_2$ are each independently a straight chain or branched chain alkyl group of $C_1$ to $C_7$, a straight chain or branched chain hydroxy alkyl group of $C_1$ to $C_7$, a straight chain or branched chain of an amino alkyl group of $C_1$ to $C_7$, a straight chain or branched chain alkoxy group of $C_1$ to $C_7$, or a hydroxy group, and $Y^-$ is $OH^-$, $Cl^-$, $Br^-$, $I^-$, $CH_3COO^-$, $NO_3^-$, or $BF_4^-$, the method comprising injecting the compound into a place to inhibit the formation of the gas hydrate and wherein the composition further comprises a solvent, wherein the solvent is water.

10. The method of claim 9, wherein $R_1$ is a methyl group, an ethyl group, or a propyl group, and $R_2$ is a butyl group, a pentyl group, a hexyl group, a heptyl group, a hydroxymethyl group, a hydroxyethyl group, or a hydroxypropyl group.

11. A gas hydrate inhibitor comprising N-hydroxyethyl-N-methylpyrrolidinium tetrafluoroborate.

* * * * *